United States Patent [19]

Cartmell

[11] 4,370,984
[45] * Feb. 1, 1983

[54] X-RAY TRANSPARENT MEDICAL ELECTRODE

[75] Inventor: James V. Cartmell, Dayton, Ohio

[73] Assignee: NDM Corporation, Dayton, Ohio

[ * ] Notice: The portion of the term of this patent subsequent to Mar. 24, 1998, has been disclaimed.

[21] Appl. No.: 246,874

[22] Filed: Mar. 23, 1981

Related U.S. Application Data

[62] Division of Ser. No. 34,394, Apr. 30, 1979, Pat. No. 4,257,424.

[51] Int. Cl.³ ............................................. A61B 5/04
[52] U.S. Cl. ................................. 128/640; 128/641; 128/803
[58] Field of Search ........................... 128/639–641, 128/643, 644, 787, 798, 802, 803

[56] References Cited

U.S. PATENT DOCUMENTS

| | | | |
|---|---|---|---|
| 3,151,619 | 10/1964 | Sullivan | 128/640 |
| 3,170,459 | 2/1965 | Phipps et al. | 128/640 |
| 3,547,104 | 12/1970 | Buffington | 128/630 |
| 3,805,769 | 4/1974 | Sessions | 128/641 |
| 3,888,240 | 6/1975 | Reinhold, Jr. et al. | 128/644 |
| 3,976,055 | 8/1976 | Monter et al. | 128/2.06 E |
| 3,977,392 | 8/1976 | Manley | 128/641 |
| 4,040,412 | 8/1977 | Sato | 128/640 |
| 4,050,453 | 9/1977 | Castillo et al. | 128/640 |
| 4,051,842 | 10/1977 | Hazel et al. | 128/640 |
| 4,082,087 | 4/1978 | Howson | 128/640 |
| 4,102,331 | 7/1978 | Grayzel et al. | 128/640 |
| 4,155,354 | 5/1979 | Rasmussen | 128/640 |
| 4,243,051 | 1/1981 | Wittemann | 128/798 |
| 4,243,052 | 1/1981 | Bailey | 128/798 |

FOREIGN PATENT DOCUMENTS

| | | | |
|---|---|---|---|
| 2271846 | 12/1975 | France | 128/803 |
| 6803290 | 9/1968 | Netherlands | 128/639 |
| 1441622 | 7/1976 | United Kingdom | 128/639 |
| 1519782 | 8/1978 | United Kingdom | 128/640 |

OTHER PUBLICATIONS

Neuman, "Flexible Thin Film Skin Electrodes . . .", DIG. 10th Int. Conf. on Med. & Bio. Eng., p. 73, 1973.
"The Shape Conforming Electrode", Med. & Bio. Eng., vol. 7, pp. 341–343, 1968.
Leask et al., "A Mult-pole Printed Circuit Electrode", The Lancet, p. 1082, 5/16/64.
Mariott et al., "Improved ECG Monitoring . . .", J. Electrocardiology, vol. 10 (2), 1977, pp. 119–122.
Sullivan et al., "A Low Mass Electrode . . .", J. Applied Psysiology, vol. 16, pp. 939–940, 1961.
Webster, "Flexible Electrodes", Med. Inst. App. & Design, pp. 245–247, 1978.

*Primary Examiner*—Lee S. Cohen
*Attorney, Agent, or Firm*—Dybvig & Dybvig

[57] ABSTRACT

The signal conducting element of a medical electrode of the type bridged to skin by electrolyte and which is required to be X-ray transparent comprises a thin layer of a conductive paint adhered to a relatively thin supporting substrate, said substrate with adhered paint extending remotely from the electrolyte-to-skin interface for circuit connection and protected by a barrier which excludes electrolyte from the remote circuit connection.

6 Claims, 5 Drawing Figures

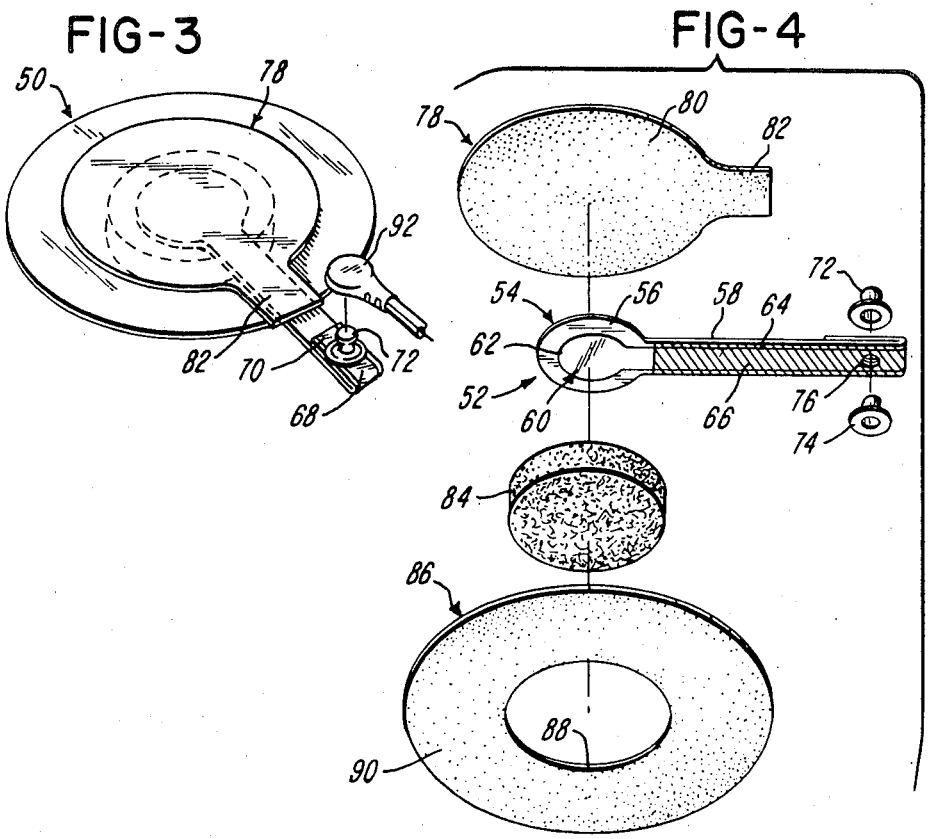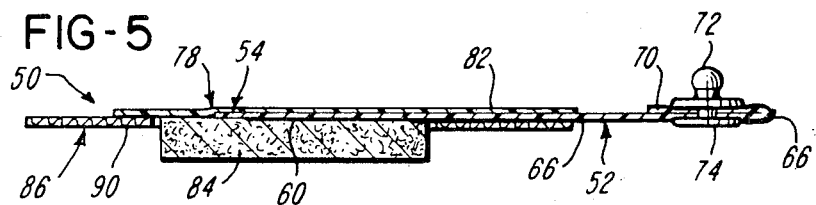

4,370,984

X-RAY TRANSPARENT MEDICAL ELECTRODE

This is a division of application Ser. No. 34,394, filed Apr. 30, 1979 for X-RAY TRANSPARENT MEDICAL ELECTRODE now U.S. Pat. No. 4,257,424, granted Mar. 24, 1981.

BRIEF SUMMARY OF THE INVENTION

A compactly assembled X-ray transparent medical electrode of the type contacted to the skin for electrocardiograph and like forms of monitoring or for stimulation utilizes a conductor member comprising a thin strip of nonconductive material having a thin layer of electrically conductive paintable material adhered to one face thereof. A first area of the adhered conductive material is adapted for contact by an electrolyte loaded sponge which is used to bridge the conductor member to the skin. A second area of the conductive material which is remote from the aforementioned first area is provided for connection of the electrode to external equipment. The conductive paintable material provides a continuously conductive layer extending from the electrolyte engaging first area to the remotely disposed second area of the conductive material. The conductor member is provided with barrier means covering a portion of the paintable conductive material between the first and second areas to limit the area of the paintable material to which the electrolyte has access and thereby minimize artifact noise attributable to migration of electrolyte to surface areas of the paintable material which have not been passivated with respect to the electrolyte. In one embodiment, the electrolyte loaded sponge is retained in position by sandwiching of the conductor member along with the electrolyte sponge between a flexible cover disc and a flexible skin contacting pad having an aperture receiving the electrolyte sponge for presenting such sponge to the surface of live skin for stimulation or monitoring purposes. In another embodiment, the electrolyte sponge is supported in contact with the paintable conductive material at the area thereof provided for electrolyte contact by adhesion of the sponge to a flexible cover member having an adhesive surface, said electrolyte sponge being encircled by an annulus of a flexible and breathable sheet material adhered on one face thereof to the flexible cover member and provided at the opposite face thereof with a pressure sensitive adhesive layer effective for attaching the electrode to the skin of a patient and in so doing effective to press the electrolyte loaded sponge firmly against the skin of a patient. By way of illustration, the second embodiment includes a snap fastener type conductor arrangement for convenient connection of the electrode to remote monitoring or stimulating equipment.

BRIEF DESCRIPTION OF THE DRAWINGS

In the drawings:

FIG. 3 is a perspective illustration of a modification.

FIG. 4 is an exploded perspective view of the modification.

FIG. 5 is a vertical section of the modification.

DETAILED DESCRIPTION

Figure 1:
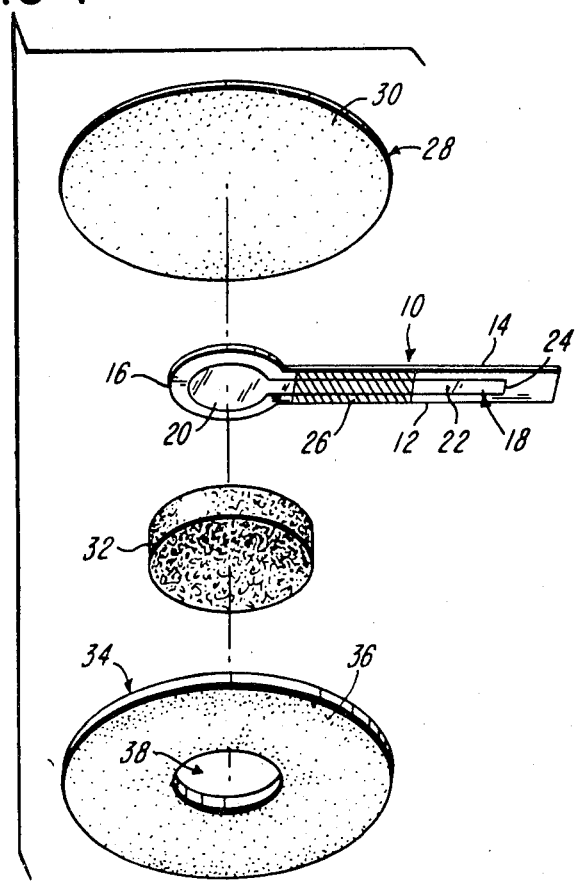
FIG. 1 is an exploded perspective view of an electrode structure in accordance with the present invention.
Figure 2:
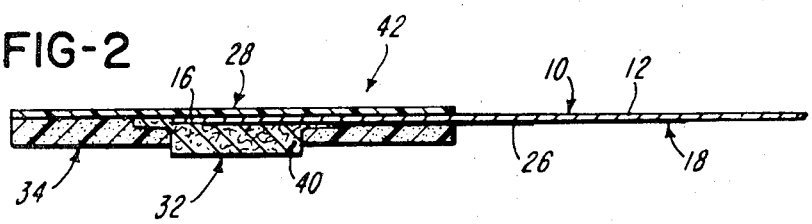
FIG. 2 is a vertical section view of the electrode structure of FIG. 1 after the assembly thereof.

Having reference to FIGS. 1 and 2, the preferred embodiment includes a signal conductor 10 which comprises a flexible, dimensionally stable, substrate 12 of a nonconductive plastic sheet material such as polyethylene terphthalate. The substrate is shaped as by die stamping to have an elongated stick portion 14 terminating at one end of the stick portion with an enlarged circular island 16. Applied to this nonconductive substrate is an electrically conductive surface layer 18, the boundaries of which are spaced inwardly from the side edges of the nonconductive substrate. The surface layer 18 thus has a circular terminal portion 20 smaller than the island 16 and, extending outwardly from the terminal portion 20 along the stick portion 14, a longitudinally disposed conductive finger 22.

The surface layer 18 comprises a layer of silver paint which is preferably applied by silk screening. As an example, the silver paint may be DuPont Conductor Composition No. 9793, a conductive paint tailored for screen printing electrical circuits onto plastic substrates. This Composition is commercially available from the DuPont Chemical Corporation. While silk screening of a commercially available compound is preferred for the formation of the conductive surface layer 18, it is to be understood that other procedures for preparation of the surface layer 18, such as brush painting, or printing, or spraying through a suitable mask may also be utilized in the practice of the present invention.

For reasons to be described, a nonconductive moisture impermeable barrier layer 26 comprising an acrylic plastic or the like is applied over the conductive surface layer 18 at that portion of the conductive finger 22 which is adjacent the terminal portion 20.

After the described preparation, the face of the signal conductor 10 which is opposite the face bearing the conductive layer 18 is pressed against an adhesive layer 30 supported by a circular plastic disc 28. The disc 28 which is preferably relatively impermeable to moisture may be a pliant plastic, such as a vinyl plastic. The exposed face of the circular island 16, together with the exposed face of the circular terminal portion 20 are then contacted by a circularly formed sponge 32. The sponge 32 is larger in diameter than the island 16 and smaller in diameter than the disc 28. The sponge 32 is retained in position by a circularly formed flexible, resilient and nonconductive foam plastic sheet or pad 34 pressed against the adhesive layer 30 so as to sandwich the sponge 32 and the signal conductor 10 between the disc 28 and the pad 34.

The pad 34 can be seen to have an adhesive layer 36 on one face thereof and a centrally located aperture 38 which is smaller in diameter than the sponge 32. Accordingly, as the pad 34 is pressed against the disc 28, the outer margin of the sponge 32 is compressed while the central portion of the sponge 32 is displaced outwardly through the aperture 38 so as to produce a pad portion 40 projecting outwardly from the adhesive coated face of the foam plastic pad 34.

It will be noted that as the pad 34 is pressed firmly against the adhesive layer 30 contained on the disc 28, the signal conductor 10 is securely positioned by reason of the back surface of the substrate 12 being adhesively engaged to the adhesive layer 30 of the disc 28 and by reason of the retention of the underlying pad 34 by such adhesive layer.

The thus mounted sponge 32 is next saturated with any suitable electrolyte, it being convenient for this purpose to introduce the electrolyte into the sponge 28 with aid of an injection device, such as a hypodermic needle.

The electrode device as thus far described is illustrated in full assembly in FIG. 2 where the assembled device has been given the reference number 42. While not illustrated, the assembled device may be protected for purposes of storage and shipment by a protective cover of a type sized to underlie the entire adhesive coated area of the pad 34 and of the type containing a recessed central portion sized to accommodate the outward projection of the pad portion 40. Such protective cover would, of course, be provided with a surface engaging the adhesive layer 36 which is of a type readily stripped from the adhesive layer 36.

The electrode device as described contains a circular terminal portion 20 which comprises a silver paint in intimate contact with the electrolyte loaded sponge 32. As understood by those skilled in the art the silver located at the surface of the silver paint will intially have a reaction to the electrolyte contacted thereto such that should the electrode then be connected to monitoring equipment an erratic signal will appear. In time, however, the silver contacted by the electrolyte will become passivated with respect to that electrolyte and a stable signal will thereafter appear on the monitor. If, however, the electrolyte should migrate to a new and thus unpassivated area of the silver paint, the signal then being monitored would again become erratic until passivation was again accomplished. In order to protect the electrode device from such signal aberration, the present invention contemplates the provision of means restricting the areas of the silver paint which are permitted to be contacted by electrolyte. Thus FIG. 1 displays a protective barrier layer 26 overlying a portion of the finger 22 adjacent the terminal portion 20. The preferred layer 26 comprises a nonconductive plastic such as an acrylate plastic painted over the finger 22 for an appreciable area as shown in FIG. 1. Alternatively, the indicated area may be covered with a pressure sensitive adhesive capable of adhering to the confronting face of the pad 34 so as to retard electrolyte migration. As a further alternative any nonconductive material capable of forming a dam across the finger 22 adjacent the terminal portion 20 may be used to effectively retard electrolyte migration.

The barrier layer 26 can be recognized as a device which divides the silver painted layer 18 into a first exposed portion for receiving a signal to a monitored by ionic conduction through the electrolyte and a second exposed portion for relaying the signal by electronic conduction for application to an external circuit, not shown. The first exposed portion comprises primarily the island 16, and, while it should be understood that all areas of the layer 18 participate in electronic conduction, the second exposed portion comprises the outward end 24 of the finger 22 where isolated from contact with the electrolyte. This outward end 24 provides a surface engageable by any electronic conduction means, not shown, which may be used to relay the signal remotely to the external circuit without regard to the nature of such electronic conduction means. Thus, precautions have been taken to retard access of the electrolyte to the outer end of the finger 22 and accordingly little opportunity exists for the development of signal artifacts of the type that could result from contact of the electrolyte to dissimilar metals.

Since whatever metal that might be used for remote transmission of the signal being monitored is protected from contact with electrolyte the signal relay means may be reusable and thus may be a permanent component of the external circuit, whereas the electrode device 42 is conveniently disposable.

An advantage to the construction of the present electrode is that the outer end of the flexible stick portion 14 can be attached to whatever signal relay means is to be employed for remote transmission without inducing any pressure on the patient to whom the electrode may have been attached. Furthermore, the stick portion 14, because flexible, will not effectively transmit external forces to which the stick portion may be exposed to the terminal portion 20 and thus forces acting on the outer end of the stick portion have only a minimal affect on the interface between the electrolyte sponge 32 and the electrically conductive surface layer 18.

An important attribute of the present invention is that the layer 18, which has been described as produced by silk screening silver paint, together with the substrate 12 can be rendered sufficiently transparent to X-ray radiation that the presence of the electrode 42 on a portion of the body, such as the chest, will not be discernable when the subject being monitored is also exposed to the X-ray radiation normally used to produce a chest X-ray photograph. In the practice of the present invention, chest X-ray transparency is attained if the substrate 12 comprises a layer of polyethylene terphthalate, such as sold under the Trademark Mylar, which is in the range of ½ mil (0.00127 cm) to 20 mils (0.0508 cm) in thickness and the silver paint layer applied to such substrate is in the range of ½ mil (0.00127 cm) to 6 mils (0.0152 cm) thick. Accordingly the combined thickness of the substrate 12 and the conductive surface layer 18 can range between 1 mil (0.00254 cm) and 26 mils (0.0660 cm).

The above indicated thickness range for Mylar represents the range of thicknesses in which Mylar is thought to be commercially available. As a practical matter, however, the thickness of the Mylar layer appears to be unimportant because the Mylar thickness is always small in relation to the amount of tissue also interposed in the path of the chest X-ray radiation even in the case of neonatal chest X-rays. Likewise, the lower thickness in the range recited for the silver paint represents the minimum thickness of silver paint that can be silk screened with commercially available equipment, and the largest thickness in the recited range is merely the maximum thickness of silver paint that can be silk screened with commercially available equipment. Thus it is thought that thicker layers of Mylar and/or silver paint may be employed in an X-ray procedure without interference to the intended use of the resultant X-ray photograph.

It has been reported that X-ray transparency obtained through use of a vacuum deposition of silver proves to be undesirable because vacuum deposited silver is not securely retained by a substrate such as Mylar. In contrast to such report, a silver paint, such as the aforementioned DuPont Conductor Composition No. 9793, is found to provide ample adhesion between the silver paint and the described Mylar substrate. Additionally, the silver paint provides the obvious convenience and economy of a painting operation as compared to a vacuum deposition technique.

While silver paint has been described as the preferred signal conducting means for use in the present invention, those skilled in the art will appreciate that other paints such as, for example, a conductive gold paint, may be employed in lieu of the silver paint. However, the experience to date with gold paint as well as paints produced with other conductive metals is that an electrocardiograph trace recorded while using silver as the conductive metal adhered by painting to the signal conductor element 10 produces a trace of greater fidelity.

The modified electrode 50 illustrated in FIGS. 3, 4 and 5 is superficially quite similar to the electrode 42, but a number of improvements embodied in the electrode 50 warrant a thorough description of this modification. The modification includes a signal conductor 52 comprising a substrate 54 supporting a paintable layer 60 of a conductive paint which is adhered to one face of the substrate. The substrate 54 which may be similar in shape to the previously described substrate 12 is again a dimensionally stable plastic sheet such as a sheet of polyethylene terphthalate. The substrate is shaped as by stamping to have a circular island 56 located at one end of a relatively narrow and elongate stick portion 58. The electrically conductive paintable layer 60 is shaped to have a circular terminal portion 62 adhered to the aforementioned island 56 and is shaped to have an elongated finger portion 64 extending integrally outward from the terminal portion 62. The finger portion 64 extends substantially the entire length of the stick portion 58 and it can be noted that the outermost end of the stick portion has been folded back on itself to produce an exposed conductive tab 68. In particular it can be noted in FIG. 4 that the conductive paint is located on the face of the major length of the stick portion 58 which is visible in FIG. 4 and when the stick portion is folded to form the tab 68, the conductive paint surface 70 on the tab 68 is placed behind the stick portion 58 so as to be exposed at the opposite side of the stick portion 58. The conductive tab 68 together with that part of the finger portion 64 over which the conductive tab has been folded are through perforated to form an aperture 76 for receipt of an eyelet 74 which is pressed into a stud 72. Since, as will be explained, the stud 72 is protected from electrolyte contact, this stud may be a conventional metallic snap fastener part. It is preferred, however, that the eyelet 74 be a non-metallic piece which may be molded from a plastic material such as polyethylene or polypropylene. Thus the stud 72 which is electrically conductive bears against the exposed electrically conductive paint surface 70 residing on the tab 68. On the other hand the eyelet 74, being a nonconductive plastic, lays harmlessly adjacent the conductive paint extending along the finger portion 64.

The face of the substrate 54 which is opposite the conductive paint layer 60 is pressed against an adhesive layer 80 applied to a pliant and relatively impermeable protective cover 78. The cover 78 which may be a vinyl plastic is generally circular in shape but departs from true circularity by reason of the presence of an outward projection 82 at the margin thereof. When the conductor member 52 is pressed against the adhesive layer 80 present on the cover 78, the conductor member is aligned lengthwise with the outward projection 82. As is evident the length of the outward projection 82 allows the conductor member 52 to be pressed into position against the cover 78 without the adhesive present on the projection 82 contacting the exposed surface 70 of the tab 68.

As was the case with the electrode 42, it is preferred that the paintable layer 60 comprise a silver paint and, to minimize signal artifacts, it is preferable that the finger portion 64 be so protected as to prevent a migration of electrolyte to unpassivated areas of the layer 60 capable of reacting chemically with the electrolyte. Thus as illustrated in FIG. 4 a substantial length of the finger portion 64 has been protected with a barrier layer 66. This barrier layer may comprise a coating of a nonconductive plastic material such as acrylate plastic or simply an adhesive layer capable of adhering to an annulus 86 to be applied over the conductor member 52 as will be more fully described. It is preferred that, whatever device may be used to form the barrier layer 66, the barrier layer extend from substantially the juncture between the finger portion 64 and the terminal portion 62 to substantially the fold which places the tab 68 under the stud 72. The nonconductivity of the barrier layer 66 is important for two purposes. One purpose, as already described, is to preclude a migration of electrolyte to unprotected areas of the conductive paint layer 60. The second purpose is to avoid artifact signals attributable to contact of the conductive paint layer 60 by the skin of a patient. Accordingly, the exposed face of the finger portion 64 appearing in FIG. 4 is coated with an insulating layer including the barrier layer 66 and the nonconductive eyelet 74, such insulation extending from substantially the terminal portion 62 to the fold at the tab 68. Of course the conductive stud 72 remains exposed but has minimal access to the patient's skin as will be more fully explained.

Upon completion of the barrier layer 66 an initially dry sponge 84 whose diameter noticeably exceeds the diameter of the island 56 is pressed against the island in such a fashion that the outer peripheral portions of the sponge adhere to the adhesive layer 80 present on the cover 78. The sponge 84 is then saturated with an electrolyte. Surrounding the sponge 84 is an annulus 86 comprising a surgical tape formed of any suitable porous and thus breathable material. The annulus 86 has a central aperture 88 of a diameter adequate to surround without contacting the circular sponge 84. The annulus 86 is adhered at one face thereof to the adhesive layer 80 present on the cover 78 and is provided at the opposite face thereof with a pressure sensitive adhesive layer 90 for attachment to the skin of a patient. FIG. 3 illustrates the side of the resulting electrode 50 which will face away from the skin when attached to a patient, and as evident the stud 72 is positioned to project away from the skin of the patient with minimal possibility of contact to the skin.

Those skilled in the art will appreciate that during periods of storage and use of the electrode 50, electrolyte applied to the sponge 84 may migrate so as to reach the interface between the annulus 86 and the barrier layer 66 with the consequence that capillary action may advance the electrolyte outwardly in the general direction of the stud 72. Those skilled in the art will further appreciate, however, that any such capillary action will be of limited effect since any outward movement of the electrolyte will terminate when the electrolyte reaches the outer periphery of the annulus 86. Thus, even though a minor amount of capillary action might occur, the extent of action is limited by the dimensions of the annulus 86 with the consequence that only a minor proportion of electrolyte will be able to migrate away from the electrolyte sponge 84.

As suggested in FIG. 3, connection of the electrode 50 to signal monitoring equipment may be conveniently made by attaching a conventional snap fastener connector 92 to the snap fastener stud 72.

Although the preferred embodiments of this invention have been described, it will be understood that various changes may be made within the scope of the appended claims.

I claim:

1. A medical electrode comprising:
an X-ray transparent conductor comprising a flexible, dimensionally stable, nonconductive plastic film, a layer of conductive silver paint adhered to one surface of said film and having a first exposed conductive portion and a second exposed conductive portion spaced from said first exposed conductive portion, and further comprising a continuous insulating covering over said paint between said exposed portions;
a gel filled sponge engaging said first exposed conductive portion; and
means securing said conductor to said sponge.

2. The electrode of claim 1 wherein said conductor has a thickness in the range of 1-26 mils, said film having a thickness in the range of ½-20 mils and said silver paint having a thickness in the range of ½-6 mils.

3. The electrode of claim 1 wherein said means securing said conductor to said sponge comprises a cover sheet having an adhesive layer engaging said conductor and said sponge.

4. The electrode of claim 1 wherein said insulating covering comprises a layer of essentially moisture impermeable material covering said layer of conductive paint between said first exposed portion and said second exposed portion.

5. The electrode of claim 4 wherein said layer of essentially moisture impermeable material comprises an acrylate resin.

6. The electrode of claim 1 wherein said means securing said conductor to said sponge comprises an adhesive.

* * * * *